(12) United States Patent
Hansen (10) Patent No.: US 9,949,587 B2
(45) Date of Patent: Apr. 24, 2018

(54) DEVICE FOR TAKING A GLOVE ON AND OFF, AND A GLOVE

(71) Applicant: Glovac ApS, Aarhus N. (DK)

(72) Inventor: Jan Erik Vest Hansen, Aarhus C (DK)

(73) Assignee: Glovac APS, Aarhus N (DK)

( * ) Notice: Subject to any disclaimer, the term of this patent is extended or adjusted under 35 U.S.C. 154(b) by 0 days.

(21) Appl. No.: 14/433,226

(22) PCT Filed: Jun. 28, 2013

(86) PCT No.: PCT/EP2013/063682
§ 371 (c)(1),
(2) Date: Apr. 2, 2015

(87) PCT Pub. No.: WO2014/056640
PCT Pub. Date: Apr. 17, 2014

(65) Prior Publication Data
US 2015/0265085 A1     Sep. 24, 2015

(30) Foreign Application Priority Data

Oct. 8, 2012   (DK) ........................ PA 2012 70614

(51) Int. Cl.
*A47G 25/80*    (2006.01)
*A47G 25/90*    (2006.01)
(Continued)

(52) U.S. Cl.
CPC ......... *A47G 25/904* (2013.01); *A41D 19/015* (2013.01); *A61B 42/00* (2016.02);
(Continued)

(58) Field of Classification Search
CPC ................. A47G 25/904; A47G 25/90; A61B 2019/046; A61B 19/045; F16K 24/04; F16K 7/14; F16K 7/16; Y10T 137/3771
(Continued)

(56) References Cited

U.S. PATENT DOCUMENTS

| 1,507,875 | A | * | 9/1924 | Weis | ........................ | D06F 43/00 |
| | | | | | | 366/279 |
| 1,938,685 | A | * | 12/1933 | Breuls | ..................... | A61B 42/50 |
| | | | | | | 223/111 |

(Continued)

FOREIGN PATENT DOCUMENTS

| AU | 199745452 B2 | 5/1998 |
| DE | 41 25 037 A1 | 2/1993 |

(Continued)

OTHER PUBLICATIONS

Translation of DK200200105U3, Vest, Jan Erik, Apparatus for using in mounting and dismounting of the elastic and/or flexible gloves, Jun. 28, 2002, translated from Google Translate Web Tool, Sep. 1, 2015.*

*Primary Examiner* — Jameson Collier
*Assistant Examiner* — Heather Mangine
(74) *Attorney, Agent, or Firm* — Muncy, Geissler, Olds & Lowe, P.C.

(57) ABSTRACT

The invention relates to a device for aiding in the taking on and off a glove of an elastic material from a hand of a user, wherein the opening of the glove is reinforced by a flexible collar, the device comprising. The device according to the invention comprises a container with an opening for receiving the glove and the hand, and with a circumferential rim for supporting the collar of the glove such that the container and the glove inserted into the container form a closed compartment. The container comprises means such as a bellow to change the volume of the container and thereby of the pressure within the container. Further, a vent is placed in the container such as to be opened by the hand from within the compartment for removing any under pressure when the container volume is increased, such that the hand inserted in a glove can be easily withdrawn from the compartment. The invention further relates to method of manufacturing a glove (Continued)

for use in such device, the method involving placing a flexible collar around the wrist of a hand model prior to dip moulding the glove. When pulling off the glove from the hand mode, turning the glove except the opening with the collar inside out, the collar forms an outwardly folded down border on the finished glove.

9 Claims, 7 Drawing Sheets

(51) Int. Cl.
    *A41D 13/08* (2006.01)
    *A41D 19/015* (2006.01)
    *B29C 41/14* (2006.01)
    *A61B 42/50* (2016.01)
    *A61B 42/00* (2016.01)
    *B29L 31/48* (2006.01)
    *A41D 19/00* (2006.01)

(52) U.S. Cl.
    CPC .............. *A61B 42/50* (2016.02); *B29C 41/14* (2013.01); *A41D 19/0089* (2013.01); *B29L 2031/4864* (2013.01)

(58) Field of Classification Search
    USPC ............................................. 223/111, 78, 80
    See application file for complete search history.

(56) References Cited

U.S. PATENT DOCUMENTS

| | | | | |
|---|---|---|---|---|
| 1,996,377 A * | 4/1935 | Hinchen | ................ | A61B 42/50 223/111 |
| 2,641,767 A * | 6/1953 | La Rosa | ............ | A41D 19/0062 2/168 |
| 2,933,102 A * | 4/1960 | Hillman | ................ | F16H 57/027 137/854 |
| 3,067,001 A * | 12/1962 | McCollum | ............. | A61B 42/00 128/898 |
| 3,695,493 A * | 10/1972 | Karr | ..................... | A47G 25/904 2/162 |
| 4,002,276 A * | 1/1977 | Poncy | .................... | A61B 42/50 206/278 |
| 4,099,270 A * | 7/1978 | Jabour | ............... | A41D 19/0058 2/168 |
| 4,275,812 A * | 6/1981 | Poncy | .................. | A47G 25/904 128/856 |
| 4,909,413 A * | 3/1990 | McCutcheon | ....... | A47G 25/904 221/1 |
| 4,915,272 A * | 4/1990 | Vlock | .................. | A47G 25/904 206/278 |
| 5,725,763 A * | 3/1998 | Bonhomme | ......... | B01D 36/001 210/188 |
| 5,868,290 A * | 2/1999 | Green, Sr. | ............ | A47G 25/904 223/111 |
| 6,021,935 A * | 2/2000 | Yonezawa | ............ | A47G 25/904 223/111 |
| 6,053,380 A * | 4/2000 | Sherrod | ............... | A47G 25/904 223/111 |
| 6,274,264 B1 * | 8/2001 | Azema | .................... | H01M 2/34 429/53 |
| 6,343,425 B1 * | 2/2002 | Sias | .......................... | A61L 2/14 34/389 |
| 6,375,034 B1 * | 4/2002 | Corbett | ................ | A47G 25/904 221/30 |
| 6,394,417 B1 * | 5/2002 | Browne | .................... | F16K 7/12 251/331 |
| 6,422,235 B1 * | 7/2002 | Persson | ............. | A61M 16/0468 128/200.26 |
| 6,516,469 B1 * | 2/2003 | Schaetzel | ............... | A41D 19/01 119/850 |
| 6,557,462 B1 * | 5/2003 | Wang | ..................... | A47J 47/10 219/732 |
| 6,752,287 B1 * | 6/2004 | Lin | .................... | A47G 19/2272 220/254.9 |
| 7,377,410 B1 * | 5/2008 | Webb | ..................... | A47G 25/904 223/111 |
| 7,434,594 B1 * | 10/2008 | Robbins | ................ | F16K 15/205 137/223 |
| 7,480,945 B2 * | 1/2009 | Knuth | ................ | A41D 19/0044 2/162 |
| 8,776,825 B1 * | 7/2014 | Bigham | ............... | F16N 31/004 137/312 |
| 9,573,740 B2 * | 2/2017 | Cannon, Jr. | ........ | B65D 81/2015 |
| 2002/0043810 A1 * | 4/2002 | Dooley | ................ | A01K 23/005 294/1.3 |
| 2005/0051217 A1 * | 3/2005 | Bastien | ................ | B60R 21/276 137/538 |
| 2005/0229287 A1 * | 10/2005 | Mattesky | ........... | A41D 19/0089 2/161.8 |
| 2005/0257839 A1 * | 11/2005 | Kaneko | .................... | F16K 24/04 137/587 |
| 2007/0062970 A1 * | 3/2007 | Agahi | .................... | A47G 25/904 222/1 |
| 2008/0073388 A1 * | 3/2008 | Saegusa | ............ | A47G 25/904 223/111 |
| 2008/0092261 A1 * | 4/2008 | Yu | ..................... | A41D 19/0089 2/16 |
| 2009/0053354 A1 * | 2/2009 | Hajduch | ................ | B29C 33/10 425/546 |
| 2011/0056938 A1 * | 3/2011 | Petrarca | ................ | B65D 90/34 220/203.01 |
| 2012/0241452 A1 * | 9/2012 | Langwald | .......... | F01M 11/0408 220/235 |
| 2014/0061525 A1 * | 3/2014 | Matalon | ................ | F16K 7/126 251/331 |
| 2016/0003365 A1 * | 1/2016 | Park | ...................... | F16K 15/148 220/212.5 |

FOREIGN PATENT DOCUMENTS

| | | |
|---|---|---|
| DK | 2002 00105 U3 | 6/2002 |
| EP | 347606 A1 | 12/1989 |
| JP | 2053902 | 2/1990 |
| WO | WO 93/04637 A1 | 3/1993 |
| WO | WO 94/18900 A1 | 9/1994 |
| WO | WO 2005/053477 A1 | 6/2005 |

\* cited by examiner

DEVICE FOR TAKING A GLOVE ON AND OFF, AND A GLOVE

FIELD OF THE INVENTION

The present invention relates to a device for aiding in taking on or off a glove, the device comprising a container with an opening for receiving a glove and means for changing the volume of the container. The invention furthermore relates to a glove for use in such device, methods for manufacturing hereof, and the system of the device and a corresponding glove.

BACKGROUND

In many types of work situations gloves are required or desired in order to reduce or remove the time the bare hands are in contact or in risk of contact with for instance chemicals, detergents, or bacteria. On the other hand, the risk of skin diseases, allergy, or skin irritations increases if the gloves are used for too long especially if the gloves are of poor quality. Furthermore, in certain work environments, the gloves are required to be taken off for instance when leaving certain rooms.

A few different kinds of apparatuses and devices are known for aiding in taking on or off gloves without having to touch the outer surfaces of the gloves while doing so.

U.S. Pat. No. 1,938,685 describes an apparatus where a disposable glove is stretched over a ring and into a chamber. An underpressure is created in the chamber thereby enlarging the glove whereby the user can more easily insert the hand into the glove. The apparatus can not be used for taking off the glove. Furthermore the way the underpressure is created makes the apparatus rather bulky and unsuitable to be moved around.

In DK BA 2002 00105 is described an apparatus comprising a chamber with a bellow which is compressed when the user sticks the gloved hand into the chamber. A non-return valve below the below allows the air to escape the chamber, so that when the hand is again moved in the direction out of the chamber, an underpressure is created, the glove becomes enlarged and the hand can be removed from the glove. This however results in the drawback that hand is difficult if not impossible to remove from the chamber with the glove on or without having to use the other hand. The apparatus is thus only suitable for taking off a glove and not for aiding in taking on a glove.

Another drawback of the known apparatus is the attachment or placement of the glove in the device either being very firm and tight but requiring an initial stretching of the glove which is undesirable in taking time and the need of two hands, or in being only loosely placed but then not always sealing sufficiently tight to the chamber to obtain the required underpressure.

DESCRIPTION OF THE INVENTION

It is therefore an object of embodiments of the present invention to overcome or at least reduce some or all of the above described disadvantages of the known devices by providing a device for aiding in both the taking on and the taking off gloves without the need of both hands and without the need of touching the outside of the gloves. It is a further object of embodiments of the invention to provide a device which may be operated by the one hand only taking on or off a glove.

It is a further object of embodiments of the invention to provide a device which may be operated fast by few and simple operations preferably manually. Yet a further objective is to provide a device suitable for use with re-usable gloves.

It is a yet further object of embodiments of the invention to provide an effective device of a minimal number of parts and which may be manufactured fastly by a minimum of operations and a low manufacturing cost.

It is a yet further object of embodiments of the invention to provide an effective manufacturing method for the manufacture of a glove for the use in such a device.

In accordance with the invention this is obtained by a device for aiding in taking on and off a glove of an elastic material from a hand of a user, wherein the opening of the glove is reinforced by a flexible collar, and where the device comprises a container with an opening for receiving the glove and the hand, the opening having a size corresponding to the size of the opening of the glove. The device comprises a circumferential rim around the container opening configured for supporting the collar of the glove such that the container and the glove inserted into the container form a closed compartment. Further, the container comprises means for changing the volume of the container operable by the hand during insertion and retraction of the hand from the container, a non-return valve placed in the container such as to allow air to be pressed out when the container volume is decreased, and a vent configured to be opened by the hand from within the compartment for preventing or reducing the establishment of an underpressure when the container volume is increased, such that the hand inserted in the glove can be withdrawn from the compartment. The invention further relates to a device for aiding in taking on and off a glove of an elastic material from a hand of a user, wherein the opening of the glove is reinforced by a flexible collar forming an outwardly folded down border on the glove, and the device comprises a container with an opening for receiving the glove and the hand, the opening having a size corresponding to the size of the opening of the glove. The device further comprises a circumferential rim around the container opening configured for supporting the collar of the glove such that the container and the glove inserted into the container form a closed compartment, and the rim comprising a conical edge surface protruding outward from the container such as to engage with the outwardly folded down border on the glove when inserted in the container. Further, the device comprises means for changing the volume of the container operable by the hand during insertion and retraction of the hand from the container, and a non-return valve placed in the container such as to allow air to be pressed out when the container volume is decreased.

In an embodiment the means for changing the volume of the container are arranged such that the container volume is reduced when a gloved hand is inserted in the container through the opening or the hand is inserted in a glove placed in the opening.

In a further embodiment the means for changing the volume of the container are arranged such that the container volume is increased when the hand is retracted from the container through the opening.

The means for changing the volume of the container may comprise a compressible bellow.

When a glove is to be taken off, the gloved hand is inserted into container, and the container is compressed reducing its volume and pressing air out of the container through the non-return valve. As the hand is then retracted from the container, the container volume starts to be increased creating an underpressure in the container and making the glove suck onto the rim. The underpressure enlarges the glove and the hand can be retracted from the glove. Hereby the glove is left in the container. The glove may be hanging in an open position thereby allowing its interior to be more effectively vented and dried by the surrounding air when not in use. Also, the container then becomes a fixed and permanent place for keeping the gloves when not in use. Furthermore, the glove is thereby placed ready to be taken on again.

When a glove is to be put on, the hand is inserted into the glove already placed in or dropped into the container. As during glove removal the container is compressed by the hand insertion and again enlarged as the hand is retracted. Then the vent is activated either automatically or manually whereby any creation of underpressure is prevented and the hand may readily be retracted from the container with the glove on. The vent is preferably operated by the hand from within the chamber such that the aid of the other hand, a foot etc is not needed.

The proposed device is advantageous in providing a means for fast and easy way to take on or off a glove, which may be operated without the need to use the other hand, operating any pedals, pressing any bottoms or the like. In this way the gloves may be taken on or off without touching the exterior of any of the gloves by the fingers or by anything else such that while taking on or off the gloves, the risk of contact with dangerous or contaminating substances or materials may be greatly reduced.

In this way the device aids in more certainly ensuring that gloves are used and worn when necessary or desirable thereby reducing the risk of spreading of bacteria as well as reducing the wear on the hands and their exposure to detergent, sterilising agents etc.

On the same time the device aids in ensuring that the gloves are used only when necessary and not for too long. Hereby the effect on the skin of moisture and heat otherwise happening by the wear of gloves is reduced, and the risk of skin diseases or skin irritations reduced correspondingly.

Further, the increased ease of the process of taking on and off the gloves may advantageously lead to the use of gloves of a higher quality with respect to durability, tear strength, and of more skin-friendly materials compared to disposable gloves for single-use. This may further improve the working environment.

A further advantage is, that the device comprises only a few minimal number of parts and may therefore be manufactured fastly by a minimum of operations and at low manufacturing costs.

A further advantage is the simplicity of the operations or motions for taking the glove on or off, and which feels very intuitive with very little or no risk of doing anything wrong also due to the simplicity and robustness of the device itself with very few moving parts, no handles or buttons etc. and with no settings or choices to be made by the user.

The rim comprising an essentially conical edge surface protruding outward from the container is advantageous in engaging with and providing a contact face for the outwardly folded down border on the glove when inserted in the container. The edge surface hereby forms a natural stop for the glove ensuring the glove is not put all the way into the container. At the same time the edge engaging with the glove initiates the reduction of the volume of the container.

Further, due to the edge surface, the elastic material of the glove lays onto the edge surface automatically forming a seal aiding in creating the underpressure of the compartment and thereby making the device more efficient during the operation of taking a glove off. Further, the conical edge surface aids in guiding the glove onto the rim and to ensure an efficient functioning of the device every time the device is used. In other words may be obtained a better fit of the glove in the container and a more tight connection of the glove against the rim ensuring a better functioning of the device. Further, the guidance of the glove into place by the conical edge surface reduces or removes any sensitivity of the device as to the exact direction of hand insertion or to any distortion or deformation of the glove collar. By an essentially conical edge surface is here meant a shape of more or less circular or oval cross section of gradually decreasing diameter or cross sectional width.

The edge surface is preferably shaped to have a smallest cross sectional width or diameter at the opening of the container. The edge surface may have an inclination between 0-60 degrees, such as in the rage of 2-30 degrees, such as about 5-15 degrees. The optimal inclination of the edge surface may depend on the inclination or shape of the collar and the outwardly folded down border of the glove. Preferably the angle of the edge surface is different from the angle of the border of the glove. Hereby is ensured that the glove may be easily removed or retracted from the container when the underpressure is fully removed or reduced. Preferably, the inclination of the edge surface is smaller than the inclination of the glove border, such as a difference of 4-20 degrees, such as approximately 8-12 degrees.

By the conical edge surface narrowing in towards the opening of the container is furthermore obtained that the device can be manufactured in fewer or simpler manufacturing step. The container may advantageously be manufactured in a plastic material by e.g. blow moulding where the opening is then cut out. Due to the conical shape of the edge surface, only the very opening of the container needs to be cut free to ensure a free passage for the hand or glove insertion without any irritating or unpleasant graters or burrs.

The means for changing the volume of the container may comprise a compressible bellow. As the container volume is reduced during its operation, the overall size of the device may be kept minimal such as of a size comparable to the size of a hand. The container may have a length in the range of approximately 20-40 cm such as 25-35 cm and a width of approximately 10-25 cm. The container may optionally be in an elongate shape such as of a cocoon or a cylinder. By the use of a bellow may effectively be obtained a considerably underpressure within the container. The bellow may be placed as a circumferential band of the container and may be of a width of 3-20 cm such as in the range of 5-12 cm.

The container comprising the bellow may be manufactured in one piece and they may be manufactured by e.g. blow moulding or plastic injection. The bellow may e.g. be of a plastic or rubber-like material. The bellows preferably have rounded corners whereby the spring-like effect, i.e. the extraction and contraction, of the bellow can be increased and the durability of the bellow can be increased.

In an embodiment the container opening comprises a conical surface for guiding the glove collar down onto the rim when inserted in the container. Hereby is by simple means obtained a better fit of the glove in the container and thereby a more tight connection of the glove against the rim. This ensures a better functioning of the device. Further, the guidance of the glove into place by the conical surface reduces or removes any sensitivity of the device as to the exact direction of hand insertion or to any distortion or deformation of the glove collar.

In an embodiment the rim comprises an edge surface protruding outward from the container such as to engage with an outwardly folded down border on the glove. Hereby is obtained an increased capture of the glove when inserted into the container. Furthermore the protruding edge surface reduces the risk of accidentally pressing the glove completely into the container when inserting the hand into the container.

In an embodiment the vent comprises a hinged lid. The vent may then simply be opened by pushing the lid out from the container surface. The lid may revert back to its closed position when no longer pushed on. A valve structure may be formed in one piece including the vent and the non-return valve. Alternatively, the valve structure may be formed as two separate pieces.

According to an embodiment, the vent comprises an elongate element of a flexible material attached to the exterior of the container at both ends. The element comprises a centrally placed member extending into the container through a venting opening, such that the member and the element closes the venting opening, and such that a movement of the member causes the element to deform and the venting opening to be open. This vent construction is advantageous in being very simple, inexpensive to manufacture, easy and fast to mount on the container, yet very effective, simple and intuitive to operate and robust. The vent may be mounted anywhere in the container but most advantageously in a region close to where the fingers inserted in the glove would be when intending to remove a gloved hand from the container. The elongate element can attain a variety of shapes such as approximately oval, shaped as a strip etc. The element can be attached to the container by glue, or by mechanical fastening means, or the like. The flexible material in between the attached ends will in its relaxed or normal undisturbed state lie onto the container surface thereby sealing the venting opening. The central member can be moved by the internal overpressure in the container caused by the reduction of the container volume or be moved for example by a finger. By simply touching or slightly pushing to the member, the element will flex or deform causing the venting opening to be unsealed and open. Hereby any pressure difference between the interior of the container and the exterior will be equalized.

The shape of the vent is advantageous in that the vent is insensitive to the precise movement of the centrally placed element. That is the user does not have to perform any specific or precise operation to activate the vent.

The centrally placed element may in one embodiment be shaped as a cylinder with a diameter which is smaller than the diameter of the venting opening. By a considerable difference in diameter between the element and the opening is ensured that even a relatively small movement of the element will cause the venting.

In an embodiment the container further comprises an injection inlet for injection of a fluid such as a cleaning, disinfection, or sterilising agent into the container. Hereby, the interior and/or the outer surface of the glove may be treated by the fluid while placed in the container. The gloves may in this way be treated such as disinfected or washed with spirits between each use.

In an embodiment the container further comprises a drain hole. Hereby any fluid dripping from the glove may easily be removed periodically and when needed.

The invention further relates to a glove comprising an opening for the insertion of a hand of a user, wherein the opening is reinforced by a collar of an essentially conical shape and forming an outwardly extending and folded down border on the glove. Such glove is advantageous in optimally fitting into the device as described in the previous. The collar ensures guiding of the glove and correct placing of the glove into the device both when to be taken on and off. Further, the collar ensures the glove to lie on the rim of the device and that a sealing of the glove onto the device can be obtained automatically. Also, the collar is advantageous in functioning as a stop when inserting a glove into the device, preventing the glove from being pushed or fall into the container chamber. The collar further allows the glove to be hanged. Hereby the glove can advantageously hang and dry when not in use.

The border may have a width of 5-25 mm such as in the range of 10-20 mm. The collar may be of an elastomer material or of a rubber material.

Further, the collar of the outwardly extending border in general functions as a drip or fluid-catcher or a gutter when a user raises his gloved hand for example during cleaning. Hereby any liquid running down the glove is stopped by the collar and prevented from running further down the arm of the user.

In an embodiment, the collar comprises an inner ring and an outer ring pressed onto the opening of the glove. Hereby the collar of the desired shape may be realised by simple and inexpensive means. Further, the ring may be attached to the glove by few simple operations which may be completely automated. The rings may be attached to the glove by simply pulling and/or stretching the glove edge over the edge of the inner ring and thereafter clicking or pressing the outer ring onto the inner ring. The outer ring may comprise a number of slits thereby making the ring more flexible and easier to be pressed down onto the inner ring.

In an embodiment the rings are coloured such as in red or blue. Hereby, gloves can be distinguished from each other also during use, aiding in improving the hygiene during cleaning. Often, different gloves must be worn when cleaning different kinds of rooms or performing specific operations. The colour marking of the gloves may then reduce the risk of using contaminated gloves outside contaminated rooms thereby reducing the risk of spreading of bacteria. Further, the devices for taking the gloves on or off may be coloured correspondingly using the same colour code.

The invention further relates to a system for aiding in taking on and off a glove of an elastic material from a hand of a user, wherein the system comprises a device as described in the above and a glove comprising an opening reinforced by a flexible collar. Advantages hereof are as given in relation to the device alone.

The invention further relates to a method of manufacturing a glove for use in a device according to any of the above, the glove comprising an opening reinforced by a flexible collar, the method comprising the steps of placing the collar around the wrist of a hand model, dipping the hand model in a bath comprising the glove material such as to cover the hand model and at least a part of the collar with the glove material, heating the hand model to vulcanize the glove material, and pulling off the glove from the hand mode, turning the glove except the reinforced opening inside out such that the collar forms an outwardly folded down border on the finished glove.

Hereby may by simple yet effective means be obtained a glove with an integrated collar for yielding a folded border of the glove. Such border and reinforcing collar may be advantageous in better providing a fit of the glove against the opening of the container and in providing an edge for engaging with the rim or edge of the container stopping or preventing the glove from being pushed completely into the container.

The border may have a width of 5-25 mm such as in the range of 10-20 mm.

The collar may advantageously be placed on a conical surface of the model hand thereby yielding a larger diameter than the opening of the glove itself.

The collar may be of flexible material compatible to the glove material for optimal attachment of the glove material to the collar during the dip moulding. The collar may be of an elastomer material or of a rubber material.

In an embodiment the collar is placed on an adapter placed to lengthen the shaft of a conventional hand model.

In an embodiment the hand model and/or adapter comprise a groove for receiving the collar. This may ease the placing of the collar and on the same time increase the accuracy of the collar placement on the hand model or adapter.

The invention further relates to a method of manufacturing a glove for use in a device according to the previous description, where the glove comprising an opening reinforced by a flexible collar. The method comprises the steps of providing a glove of an elastic material, providing a collar, and fixating an opening edge of the glove to the collar such that the collar forms an outwardly extending and folded down border on the finished glove.

In an embodiment the collar comprises an inner ring and an outer ring, and the method comprises fixating the collar to the glove by pressing the inner ring and outer ring together with the opening edge of the glove in between. The advantages hereof are a described above. Further, the fixating of the collar may in this way be performed by after mounting or retrofitting on conventionally produced gloves. Any commercially available gloves may in this way be provided with a collar of the desired shape, shape, flexibility and colour matching the circumstances and specific needs.

In an embodiment the collar is fixated to the glove by glue, which provides for a simple yet effective manufacturing method of low cost. The collar may hereby likewise be retrofitted to the already produced gloves.

BRIEF DESCRIPTION OF THE DRAWINGS

In the following different embodiments of the invention will be described with reference to the drawings, wherein.

DETAILED DESCRIPTION OF THE DRAWINGS

Figures 1A, 1B:
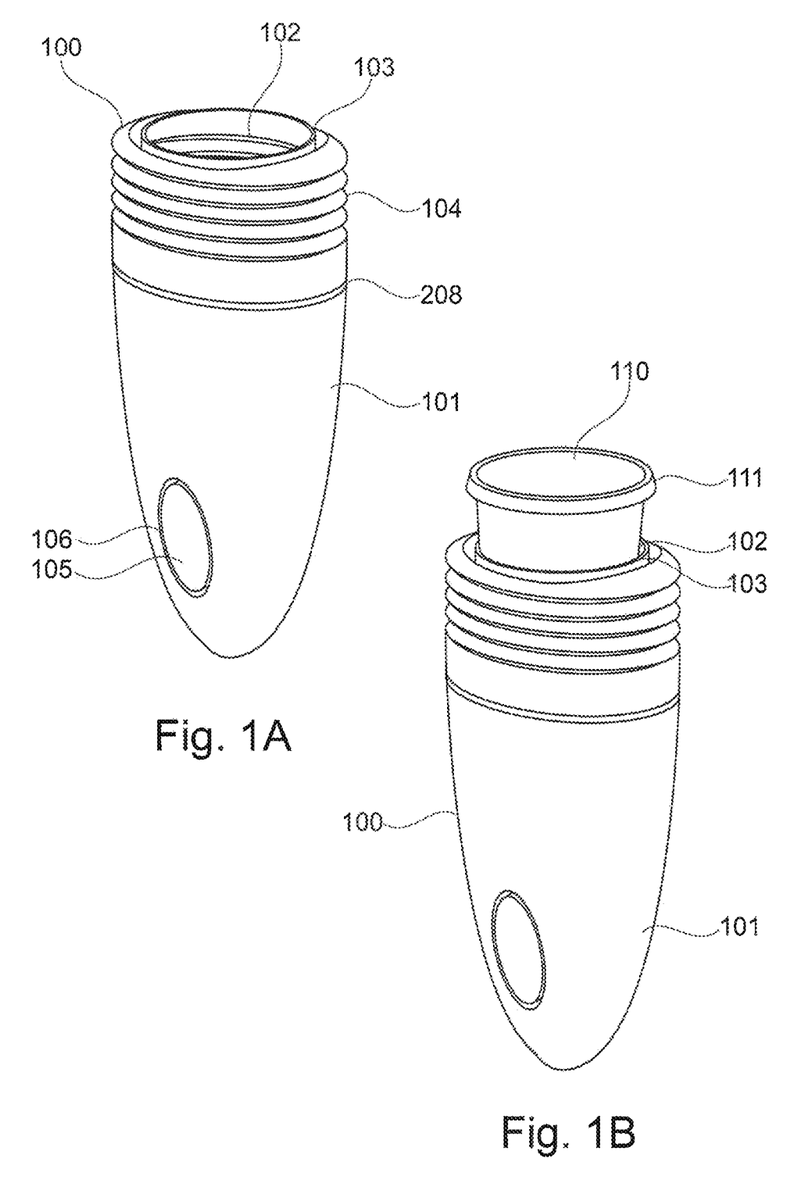
FIG. 1A illustrates an embodiment of a device for taking gloves on and off with a glove partly inserted as seen in a perspective view.
FIG. 1B illustrates the device of FIG. 1A with a glove partly inserted into the container.

FIG. 1 shows an embodiment of a device, 100 for aiding in taking on and off a glove 110 of an elastic material from a hand of a user according to the invention and as seen in a perspective view. The device 100 comprises a container 101 with an opening 102 through which the glove and the users hand is inserted. The same device is shown in FIG. 1B with a glove 110 halfway inserted into the container. A rim 103 around the circumference of the opening 102 acts to support the collar 111 of the glove, such that the glove when placed in the container rests or lies against the rim 103. When the users hand is put into or inserted in the glove, or when a hand wearing a glove is inserted into the container, the bellow part 104 of the container is compressed and the air is pressed out of the container through the non-return valve 105 (shown in more detail in later figures). As the hand is again removed, the bellow is again enlarged and an underpressure created within the container, enlarging the glove and enabling the hand to be removed from the glove. If the glove is to be taken on, a vent 106 in the container is activated and opened preferably simply by the hand from within the container. Hereby the underpressure is removed and the glove stays on the hand when removed and retracted from the container. In the embodiment of FIGS. 1A and B the vent is made in one piece with the non-return valve.

Figure 2:
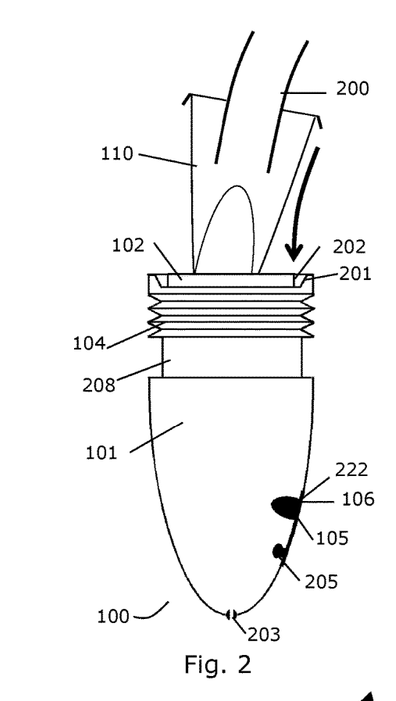
FIG. 2 illustrates an embodiment of the device as seen in a cross sectional view from a side.

FIG. 2 shows another embodiment of the device in a cross sectional view. Here, the opening 102 of the container 101 comprises a conical surface 201 with a smaller diameter towards the interior of the container. This conical shape aids the glove in being guided down to rest or lie against the rim 103 of the opening. This improves the fitting of the glove into the container such that the operating of the bellow 104 and changing of container volume may more effectively yield the desired pressure change within the container. Furthermore, the rim here comprises an edge 202 protruding outward from the container (upwards in the figure) such as to engage with an outwardly folded down border 401 on the glove 110 as may be seen in more detail in FIG. 5.

The folded down border of the glove comprises a collar 111 acting to reinforce the glove opening. The collar may furthermore act to maintain the overall shape of the glove opening for such that is easier inserted onto the rim 103 of the container opening. The folded down border of the glove may also be advantageous in preventing fluid from running from the gloved hands and down the arms 200 when working.

The device shown in FIG. 2 comprises an injection inlet 203 through which a fluid may be sprayed into the chamber e.g. for disinfecting or cleaning the glove or the gloved hand. The container may also comprise a drain hole (not shown) which may be opened for the container to be emptied of any fluid. In FIGS. 2 and 3A-D the non-return valve 105 and vent 106 is shaped as a hinged lid-like structure 222 of a resilient material press fit into a hole 205 in the container.

The container may optionally (as shown in FIG. 2) comprise a groove 208 for a fastening member to fasten the device to e.g. a cleaning cart, a rack, a wall or the like.

FIGS. 3A-D illustrate the device during the operating situation of glove removal. FIGS. 4A-D correspondingly illustrate the operation of taking on a glove. The glove optionally with a hand 200 inside is outlined in the figures by 110.

Figures 3A, 3B:
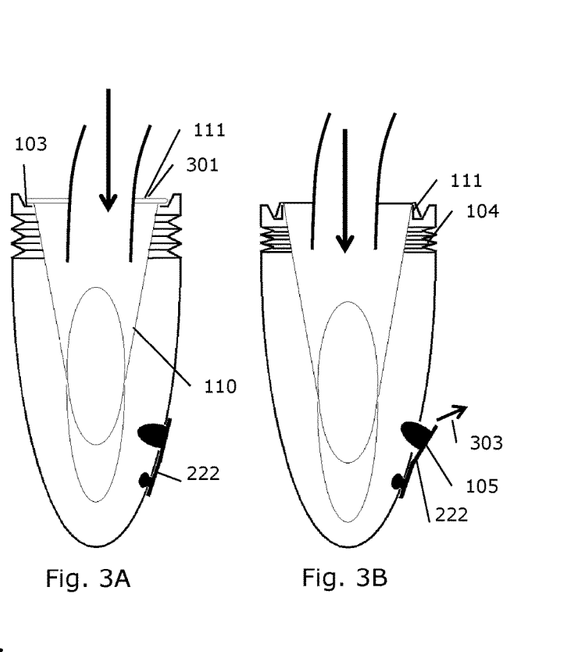
FIGS. 3A-3D illustrate the operation of taking a glove off using an embodiment of the device.

In the embodiment of FIG. 3A the collar 111 of the glove 110 is shaped as a ring 301 which when placed in the container rests against a rim 103 of a little smaller dimension. In FIG. 3A the container is shown in its still uncompressed state with a gloved hand inserted in the container. In FIG. 3B the gloved hand is pushed further into the container, and the bellow 104 is compressed, air leaving the chamber through the non-return valve 105 as illustrated by the arrow 303.

Figure 3C:
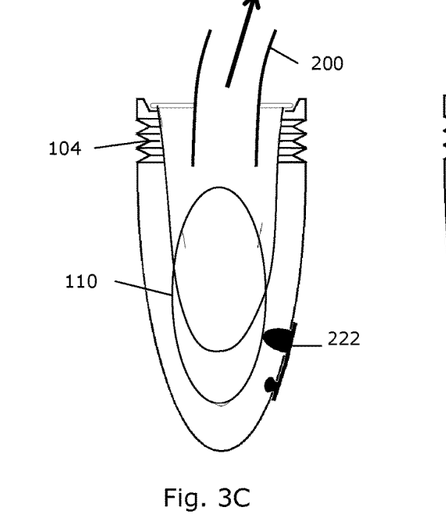
Figure 3D:
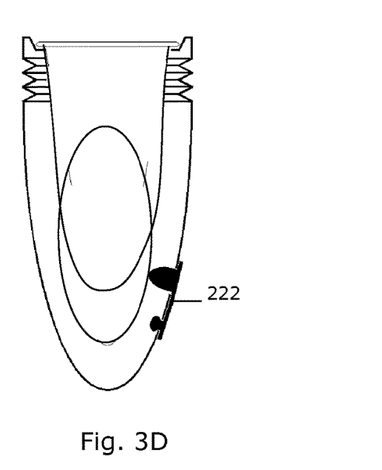
Figure 4A:
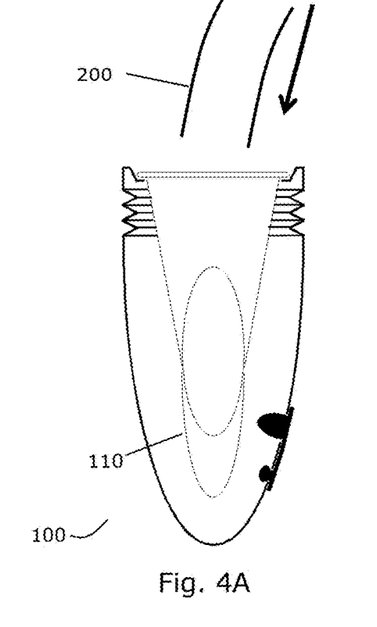
FIGS. 4A-4D illustrate the operation of taking a glove on using an embodiment of the device.
Figure 4B:
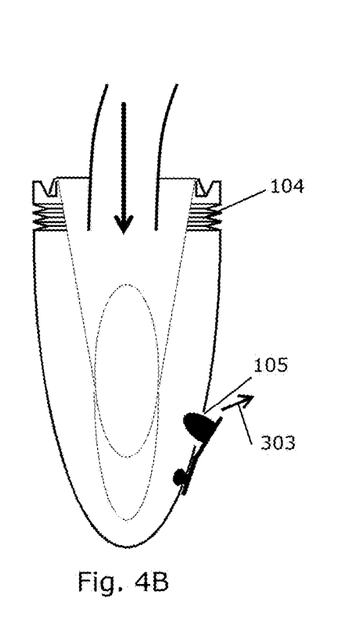
Figure 4C:
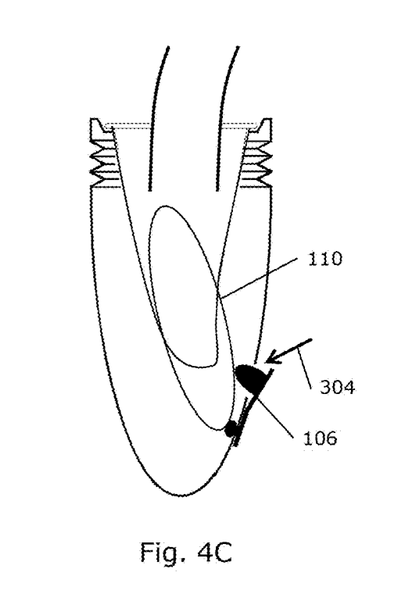
Figure 4D:
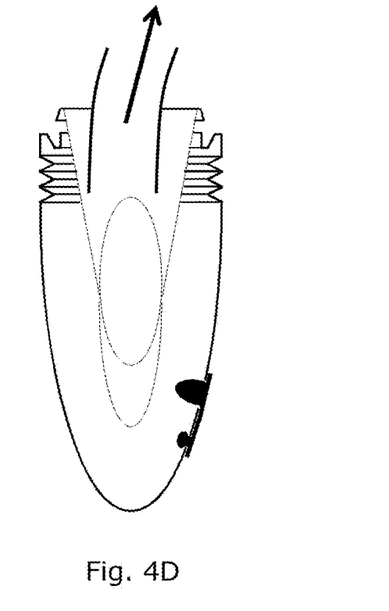

If the glove is to be taken off, the hand is extracted and the bellow is thereby enlarged (FIG. 3C). This causes the glove to be sucked more firmly onto the rim, and the glove to be enlarged by the underpressure within the container as outlined in FIGS. 3C and D. The hand can then be very easily retracted from the enlarged glove, FIG. 3D. Advantageously the glove can be left hanging, where it can dry without getting in contact with anything else.

Figure 5:
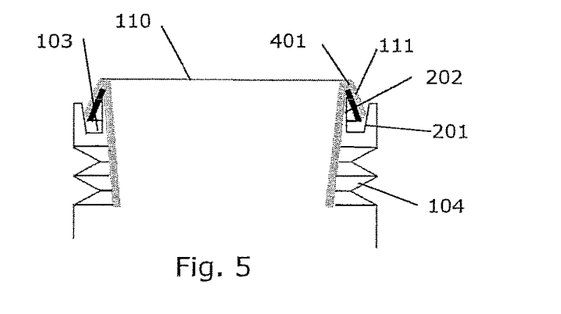
FIGS. 5 and 6 illustrate different embodiments of the engagement of a glove with the opening of the container in a larger detail.
Figure 6:
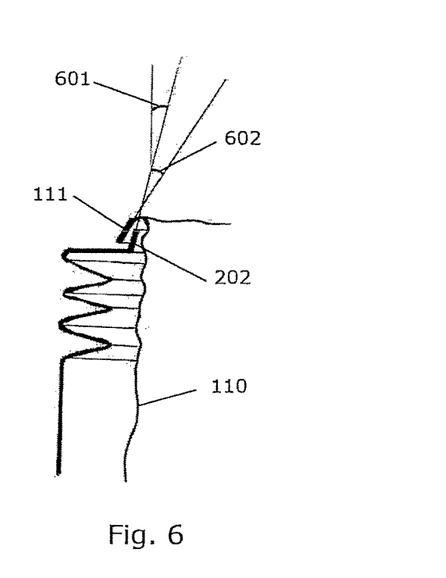
Figures 7A, 7B, 8:
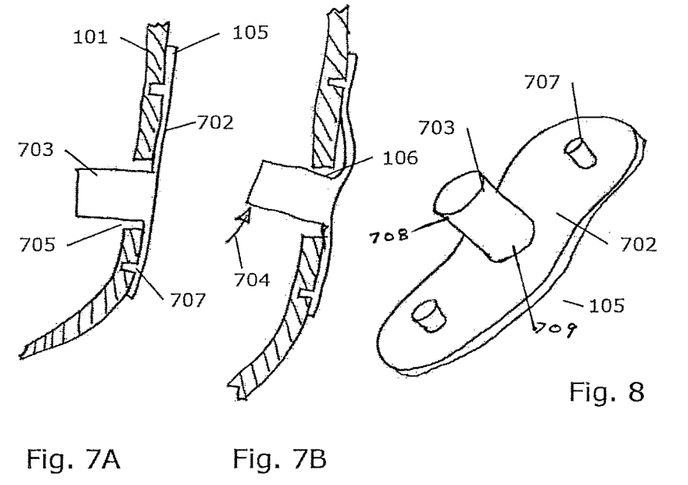
FIGS. 7A-B and 8 show sketches of the functioning of an embodiment of a vent according to the invention.

FIGS. 4A to D illustrate the situation of the glove to be taken on. The hand 200 is inserted into the glove 110 positioned the container (FIG. 4A) and the as before the bellow is compressed and an underpressure is created within the compartment, FIG. 4B. If the hand is then merely retracted, the glove will stay in the container due to the underpressure and the other hand would be needed to loosen the glove from the rim. Instead the vent 106 is opened preferably by the gloved hand from inside the container allowing air to enter the container as illustrated by arrow 304, FIG. 4C. The glove is thus not sucked onto the rim although the bellow is extracted as the hand is pulled out, and the hand can be retracted with the glove on, FIG. 4D. FIGS. 5 and 6 illustrate different embodiments of the engagement of a glove with the opening of the container in a larger detail. The figures show the glove 110 with the collar 111 engaging with the rim 103 which comprises an edge surface 202. In the embodiment of FIG. 5, the edge surface is approximately perpendicular to the rim 103 and the longitudinal direction of the container. In FIG. 6, the edge surface 202 is approximately conical narrowing in towards the opening of the container. The edge surface is here angled differently 602 than the collar 111 of the glove 110. The edge surface may be angled around 5-15 degrees to the glove collar. Hereby the glove is guided onto the rim of the container and improves the sealing of the glove to the container. This makes the device more effective for the removal and taking on of gloves. Further the difference in angle ensures that the gloves can be more easily released from the rim of the container again, FIGS. 7A and B and FIG. 8 show sketches of an embodiment of the vent 106 according to the invention. In FIGS. 7A-B the vent is shown in a cross-sectional view as attached to the exterior of the container 101 and in its closed state and its open configuration, respectively. The vent 106 comprises an elongate part 702 of a flexible material attached to the container near both its ends by fastening elements 707 clicked into corresponding holes in the container wall. A central element 703 includes a proximal end 708 connected to the elongate part 702 and a distal end 709 extending toward and protruding into the container. When undeformed as shown in FIG. 7A, the element 702 together with the central member 703 seals the venting opening 705. If the central member is moved, 704, for example by a pressure difference or by a finger, the element 702 bends, and the venting opening is unsealed.

FIG. 8 shows a sketch of the elongate element 702 of the vent 106 in a perspective view.

FIGS. 9A to D illustrate different steps in a manufacturing process of a glove suitable for the use in a device as described in the above. The finished glove 110 shown in part in FIG. 9D comprises a collar 111 reinforcing the opening of the glove through which the hand is inserted. The glove may be manufactured by placing a collar 111 on the shaft or around the wrist of the hand model 500. In the figures only the upper part of the hand model is shown continuing downwards to form the hand itself and the fingers.

Figure 9A:
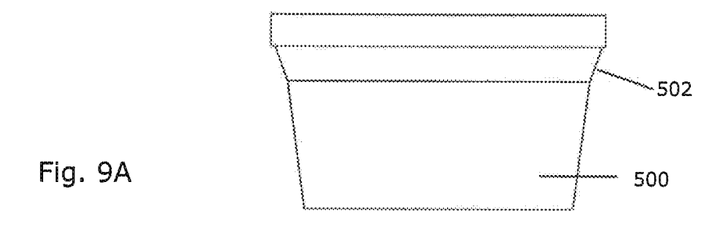
FIGS. 9A-D illustrate an embodiment of the dip moulding process of a glove.
Figure 9B:
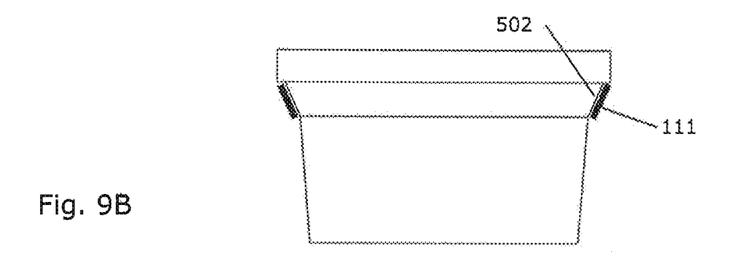
Figure 9C:
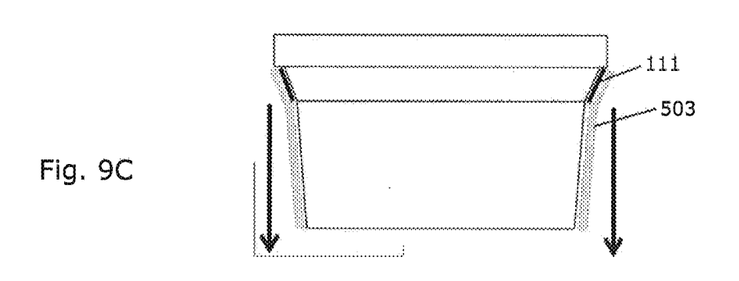
Figure 9D:
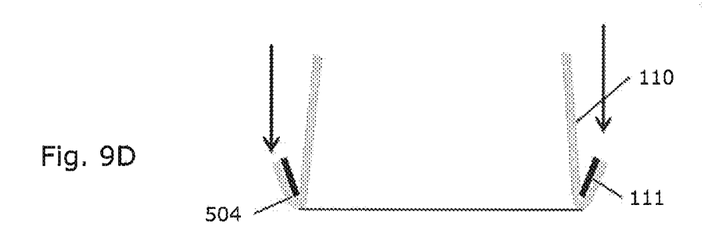

The collar 111 is here placed on a conical surface 502. The hand model is dipped and covered with the glove material 503. The model may be dipped multiple times optionally in different materials. When dried and vulcanized, the glove is pulled off the model, FIG. 9C, and turned inside out except from the part reinforced by the collar. The border 504 of the glove thereby remains bended down as shown in FIG. 9D where is illustrated the shape of shaft-part of the glove when pulled off the hand model.

Figure 10:
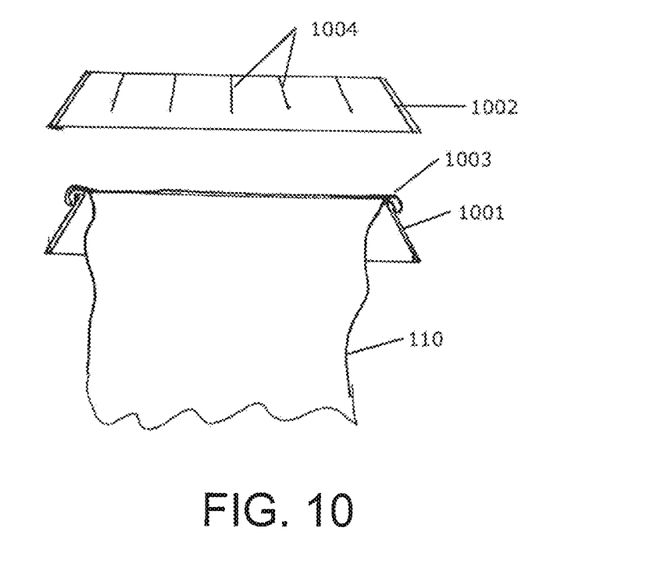
FIG. 10 illustrates an embodiment of the glove collar, FIGS. 11A and B shows the inner and outer for the glove collar in a perspective and a side view, respectively, and FIGS. 12A and B show an embodiment of a container and its attachment.

FIG. 10 illustrates an embodiment of the glove 110 with a collar 111 which is here formed by an inner ring 1001 and an outer ring 1002. Both these rings are approximately conical in shape. The glove may be manufactured by stretching the edge 1003 of the glove out over the edge of the inner ring 1001 and then pressing or clicking the outer ring 1002 onto the inner ring. The outer ring 1003 may optionally comprise a number of slits 1004 to increase its flexibility and ability to be pressed onto the inner ring and the glove edge.

Figures 11A, 11B:
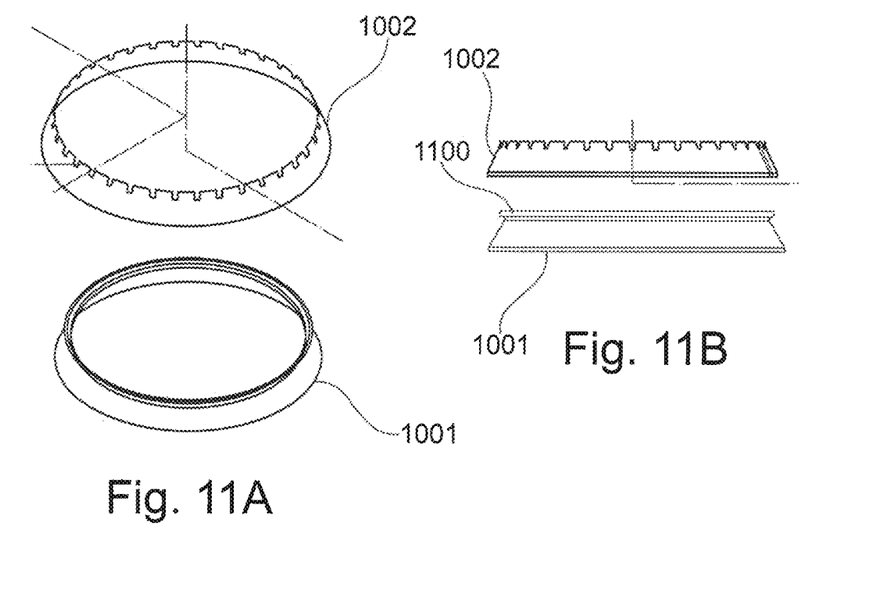

The geometry of an embodiment of the inner and outer rings are shown in FIGS. 11A and 11B in a perspective and a side view, respectively. The diameter of the outer ring may be slightly larger than the diameter of the inner ring. The inner ring may comprise a bent edge 1100 for the glove edge to be hold onto and stretched over.

Figure 12A:
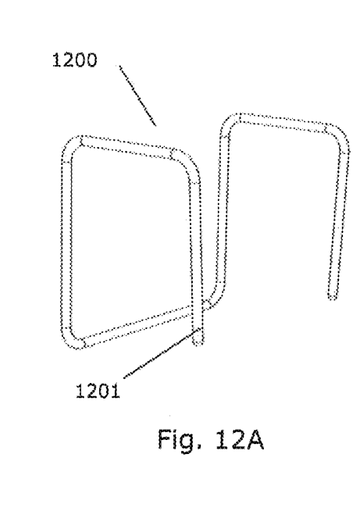
Figure 12B:
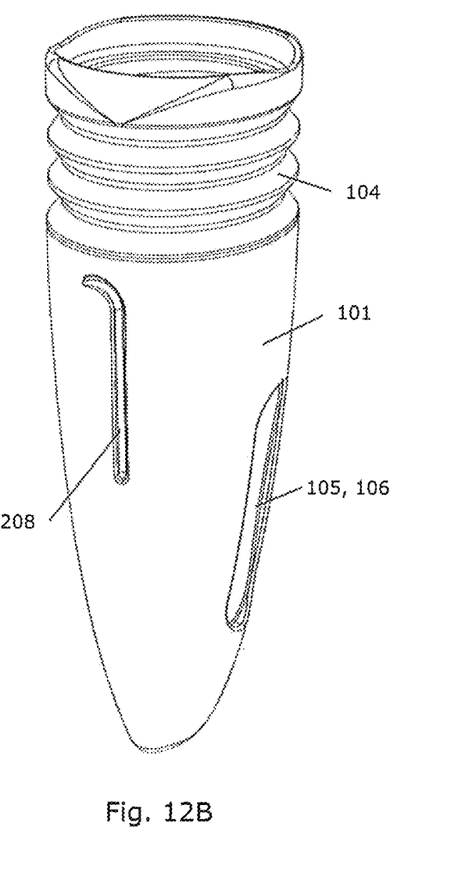

In FIG. 12 is illustrated a system for mounting a container 101 according to the invention. The container as shown in FIG. 12B on either side comprises a groove 208 for receiving the legs 1201 of the bracket 1200 so that the container is held in place by the bracket. The bracket may then be fastened to e.g. a cleaning cart, a rack, a wall or the like. The container 101 can then easily and quickly be released from the brackets for example to be cleaned or exchanged.

While preferred embodiments of the invention have been described, it should be understood that the invention is not so limited and modifications may be made without departing from the invention. The scope of the invention is defined by the appended claims, and all devices that come within the meaning of the claims, either literally or by equivalence, are intended to be embraced therein.

The invention claimed is:

1. A device configured for aiding in taking on and off a glove of an elastic material from a hand of a user, wherein an opening of the glove is reinforced by a flexible collar, the device comprising:
   a container with an opening configured for receiving the glove and the hand, the opening having a size corresponding to the size of the opening of the glove,
   a circumferential rim around the container opening configured for supporting the collar of the glove such that the container and the glove inserted into the container form a closed compartment,
   a compressible bellow arranged to change the volume of the container operable by the hand during insertion and retraction of the hand from the container,
   a valve structure including an elongated element and a projecting member, the projecting member having a proximal end and a distal end, the proximal end being connected to the elongated element and the distal end extending toward an interior of the container, the valve structure acting as a non-return valve to allow air to be pressed out when the container volume is decreased, and the valve structure also acting as a vent structure to be manually opened by a direct movement of the projecting member by the hand from within the compartment allowing an airflow into the container for preventing or reducing the establishment of an underpressure when the container volume is increased, so that the hand inserted in the glove can be withdrawn from the compartment.

2. The device according to claim 1, wherein the rim comprises an edge protruding outward from the container and configured to engage with an outwardly folded down border on the glove.

3. The device according to claim 1, wherein the compressible bellow is arranged such that the container volume is reduced when a gloved hand is inserted in the container through the opening or the hand is inserted in the glove placed in the opening.

4. The device according to claim 1, wherein the compressible bellow is arranged such that the container volume is increased when the hand is retracted from the container through the opening.

5. The device according to claim 1, wherein the container opening comprises a conical surface for guiding the glove collar down onto the rim when inserted in the container.

6. The device according to claim 1, wherein the valve structure is shaped as a hinged lid.

7. The device according to claim 1, wherein the elongated element is a flexible material attached to the exterior of the container at both ends of the elongated element, the projecting member is a centrally placed member extending into the container through a venting opening, such that the element closes the venting opening, and such that a movement of the projecting member causes the element to deform and the venting opening to be open.

8. The device according to claim 1, wherein the container further comprises an injection inlet for injection of a fluid into the container.

9. A system for aiding in taking on and off the glove of the elastic material from the hand of a user, wherein the system comprises the device according to claim 1, and the glove comprising the opening of the glove reinforced by the flexible collar.

* * * * *